US00PP12474P2

(12) United States Plant Patent
Noodelijk

(10) Patent No.: US PP12,474 P2
(45) Date of Patent: Mar. 19, 2002

(54) CHRYSANTHEMUM PLANT NAMED 'HALIFAX YELLOW'

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 09/561,936

(22) Filed: May 1, 2000

(51) Int. Cl.[7] ..... A01H 5/00
(52) U.S. Cl. ..... Plt./295
(58) Field of Search ..... Plt./295

*Primary Examiner*—Bruce R. Campell
*Assistant Examiner*—Annette H. Para
(74) *Attorney, Agent, or Firm*—Parkhurst & Wendel, LLP

(57) ABSTRACT

A Chrysanthemum plant named "HALIFAX YELLOW" characterized by its large sized blooms with yellow ray-florets and a green-yellow cushion center disc florets.

2 Drawing Sheets

RELATED CULTIVARS

"HALIFAX YELLOW" is related to HALIFAX (U.S. Plant patent application Ser. No. 09/561,965). "HALIFAX YELLOW" is a color mutant of HALIFAX.

BACKGROUND OF THE INVENTION

"HALIFAX YELLOW" is a product of a breeding and selection program which had the objective of finding color mutants of HALIFAX. The new plant of the present invention comprises a new and distinct cultivar of chrysanthemum plant that is a natural occuring sport of a parent chrysanthemum HALIFAX. A comparison with Parent chrysanthemum HALIFAX is also made in this application. The new cultivar was discovered as a whole plant mutation in June 1998 by Rob Noodelijk in a controlled environment (greenhouse) in Rijsenhout Holland. The first act of asexual reproduction of "HALIFAX YELLOW" was accomplished when vegetative cuttings were taken from the initial selection in September 1998 in Rijsenhout Holland.

SUMMARY OF THE INVENTION

The present invention is a new and distinct variety of chrysanthemum bearing large sized blooms with yellow ray-florets and green-yellow disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
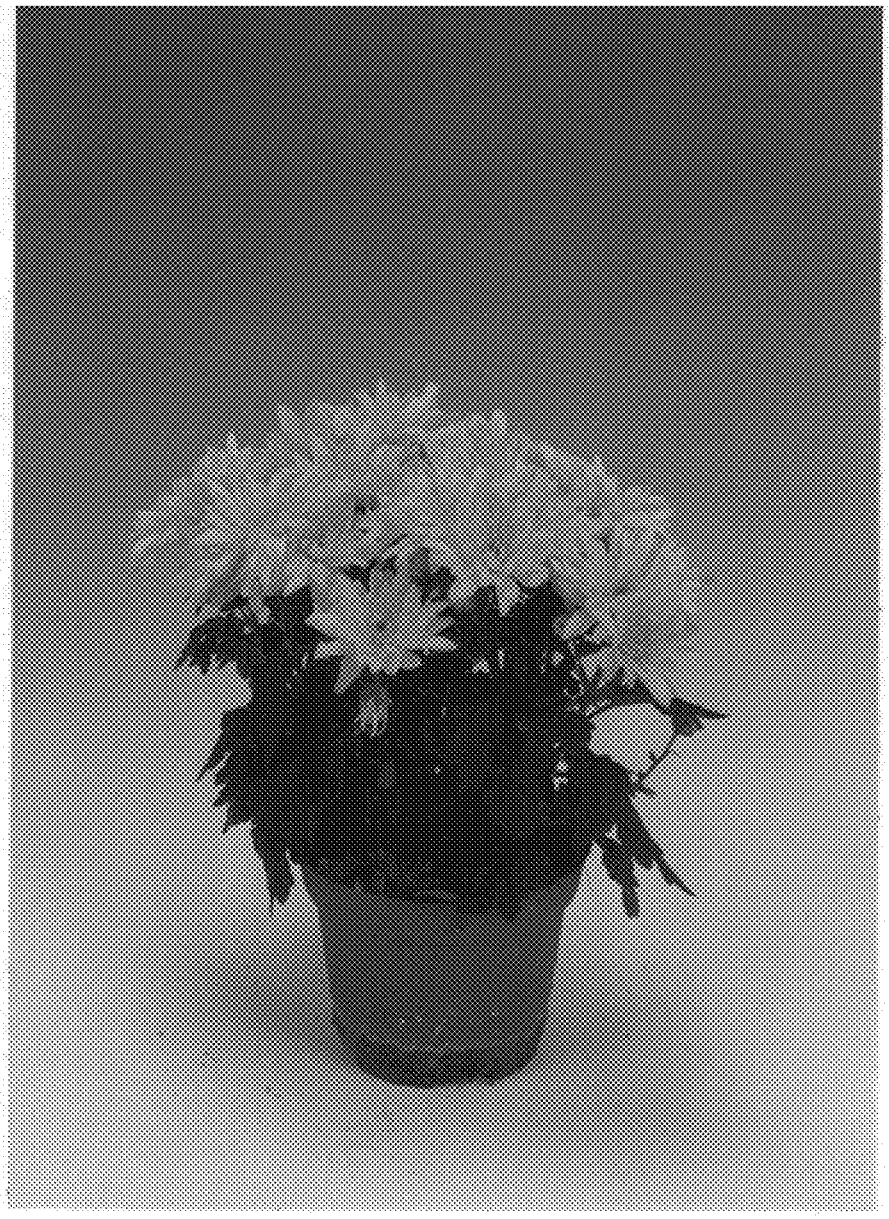
FIG. 1 shows a plant of the cultivar in full bloom.
Figure 2:
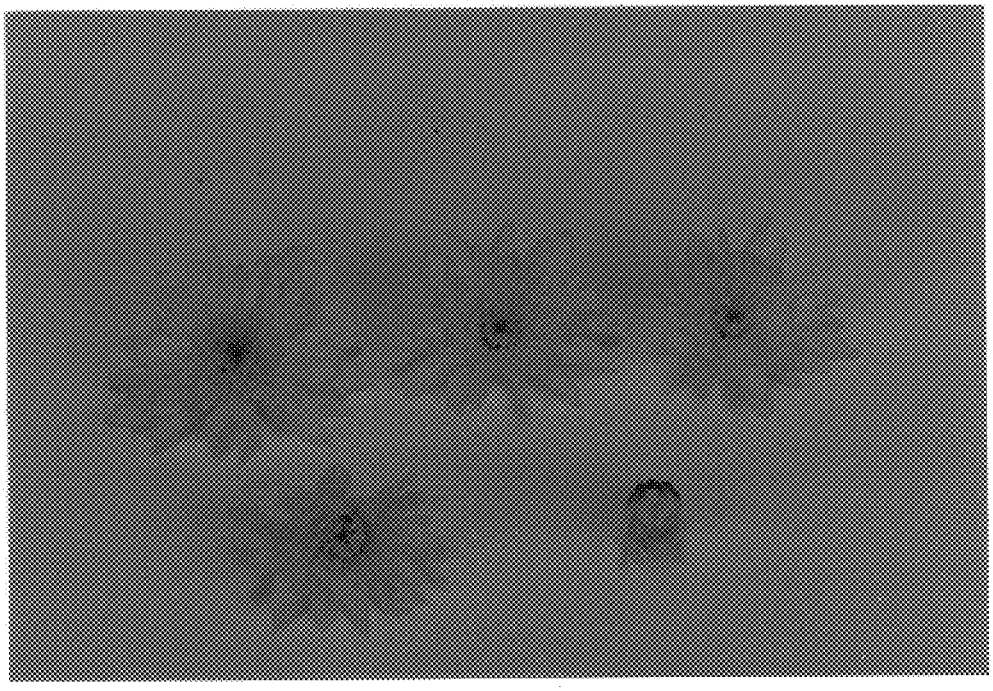
FIG. 2 shows the various stages of bloom of the new cultivar.
Figure 3:
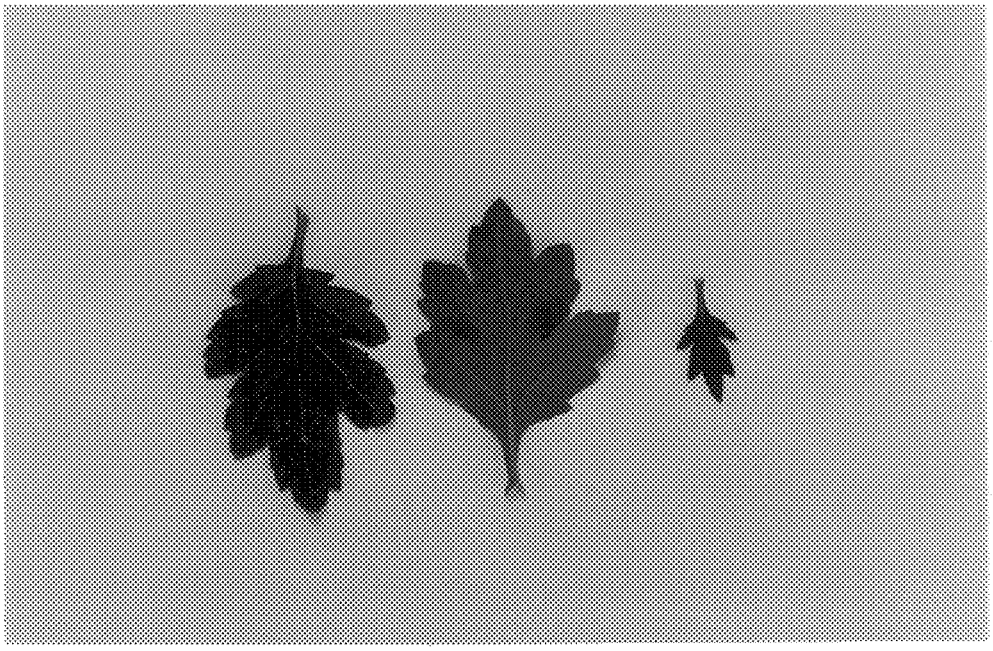
FIG. 3 shows the various stages of foliage and petiole of the new cultivar.

This new variety of chrysanthemum is of the botanical classification Dendranthema grandiflora. The observations and measurements were gathered from 64 days plants grown in a greenhouse in Rijsenhout Holland in a photo-periodic controlled crop under conditions generally used in commercial practice. The greenhouse temperatures during this crop were at day-time between 18° C. and 25° C. and at night 20° C. The photo-periodic response time in this crop was 55 days after an average of eight long days. After this long day period to flowering growth retardants were applied 6 times in an average dose of 1.5 gram/liter water. No tests were done on disease or insect resistance or susceptibility. This new variety produces large sized blooms with yellow ray-florets and a green-yellow cushion center disc-florets blooming on the plant for 5 weeks. This new variety of chrysanthemum has been found to retain its distinctive characteristics throughout successive propagations however the phenotype may vary significantly with variations in environment such as light intensity and temperature. To show the phenotype as described "HALIFAX YELLOW" can be planted without assimilation lightning (high pressure sodium lamps) between week 50 and week 40 of the next year under greenhouse conditions in Holland. With assimilation light (minimum level 2500 lux) it can be planted year round under greenhouse conditions in Holland.

From the cultivars known to inventor the most similar existing cultivar in comparison to "HALIFAX YELLOW" is HALIFAX. When HALIFAX and "HALIFAX YELLOW" are being compared the following differences and similarities are noticed: The difference of HALIFAX and "HALIFAX YELLOW" is the ray-floret color. "HALIFAX YELLOW" is yellow, HALIFAX is white. For this characteristic "HALIFAX YELLOW" has been selected out of HALIFAX. All other characteristics of HALIFAX and "HALIFAX YELLOW" are similar. Inventor does not know any other commercial available variety that is comparable with "HALIFAX YELLOW".

The following is a description of the plant and characteristics that distinguish "HALIFAX YELLOW" as a new and distinct variety. The color designations are taken from the plant itself. Accordingly, any discrepancies between the color designations and the colors depicted in the photographs are due to photographic tolerances. The color chart used in this description is: The Royal Horticultural Society color chart, edition 1995.

Botanical Description of CULTIVAR "HALIFAX YELLOW"

Bud:
*Size.*—Large; Cross-section 1.5 cm height 1.5 cm.
*Outside color.*—Yellow 3 B.
*Involucral bracts.*—2 rows, length 7 mm, width 3 mm.
*Involucral bracts among disc-florets.*—Not present.
*Involucral bracts color.*—Yellow-green 147 B.

Bloom:
*Type.*—Anemone.
*Height.*—Medium high.
*Size.*—Large.
*Fully expanded.*—7.0 cm.
*Number of blooms per branch.*—Approx. 4–5 blooms per branch.
*Performance on the plant.*—5 weeks.
*Seeds.*—Not produced.
*Fragrance.*—Typical chrysanthemum.

Color:
*Center of the flower* (*disc-florets*).—Immature Yellow-orange 15 A with yellow-green 146 C in the center, Mature Yellow-orange 146 1 D with a small green center.
*Color of upper surface of the ray-florets.*—Yellow 7 A.
*Color of the lower surface of the ray-florets.*—Yellow 7 D.
*Tonality from distance.*—A pot mum with large semi-double yellow flowers and a green-yellow disc.
*Discoloration of color.*—To yellow 6 C, the center to yellow-orange 146 D with a small green center.

Ray florets:
*Texture.*—Upper and under side smooth.
*Number.*—42–45 (3 rows).
*Cross-section.*—Flat.
*Longitudinal axis of majority.*—Straight.
*Length of corolla tube.*—Short.
*Ray-floret margin.*—Entire.
*Ray-floret length.*—3.4–3.7 cm.
*Ray-floret width.*—0.9–1.1 cm.
*Ratio length/width.*—Medium.
*Shape of tip.*—Dentate.

Disc florets:
*Disc diameter.*—2.5 cm.
*Distribution of disc florets.*—Numerous clearly visible at all stages of flowering.
*Shape.*—Petaloid.
*Color.*—Yellow-orange 15 A, yellow-green 146 C at the tip.
*Receptacle shape.*—Domed raised.

Reproductive organs:
*Stamen* (*present in disc florets only*).—Green, thin, 4 mm in length.
*Number of stamen.*—Grown, together as one.
*Stamen color.*—Yellow-green 144 B.
*Pollen.*—None.
*Pollen color.*—Not applicable.
*Styles* (*present in both ray and disc florets*).—Green, thin.
*Style color.*—Yellow-green 144 B.
*Style length.*—5 mm.
*Stigmas.*—Green-yellow.
*Stigma width.*—2 mm.
*Ovaries.*—Enclosed in calyx.

Plant:
*Form.*—A pot mum meant for indoor use.
*Growth habit.*—Spreading.
*Growth rate.*—Moderate.
*Height.*—23–25 cm.
*Width.*—25–27 cm.
*Stem color.*—Yellow-green 147 B.
*Stem strength.*—Strong.
*Stem brittleness.*—Absent.
*Stem anthocyanin coloration.*—Absent.
*Length of lateral branch.*—From top to bottom 12–13 cm.
*Lateral branch, attachment.*—Strong.
*Branching.*—Normal with 3–4 breaks after pinching.
*Flowering response* (*photo-periodic controlled crop, not natural season*).—55 days.

Foliage:
*Color.*—Upper side green 139 A Under side yellow-green 146 A.
*Size.*—Large; length 7.0 cm, width 5.0 cm.
*Quantity* (*number per lateral branch*).—7–9.
*Shape.*—Oval.
*Texture upper side.*—Glabrous.
*Texture under side.*—Pubescent.
*Venation arrangement.*—Palmate.
*Shape of the margin.*—Serrated.
*Shape of the base of sinus between lateral lobes.*—Acute.
*Margin of sinus between lateral lobes.*—Diverging.
*Shape of base.*—Rounded.
*Apex.*—Mucronate.

Differences with the comparison Varieties

| | "HALIFAX YELLOW " | "HALIFAX" |
|---|---|---|
| Ray-floret color | Yellow 7a | White 155 D |

I claim:

1. A new and distinct variety of chrysanthemum plant as described and illustrated.

* * * * *